US012745904B2

(12) United States Patent
Frey

(10) Patent No.: US 12,745,904 B2
(45) Date of Patent: Sep. 29, 2026

(54) SYSTEM AND METHOD FOR MEASURING AND CORRECTING ASTIGMATISM USING LASER GENERATED CORNEAL INCISIONS

(71) Applicant: Lensar, Inc., Orlando, FL (US)

(72) Inventor: Rudolph W. Frey, Winter Park, FL (US)

(73) Assignee: Lensar, Inc., Orlando, FL (US)

(*) Notice: Subject to any disclaimer, the term of this patent is extended or adjusted under 35 U.S.C. 154(b) by 753 days.

(21) Appl. No.: 17/375,039

(22) Filed: Jul. 14, 2021

(65) Prior Publication Data

US 2022/0175244 A1 Jun. 9, 2022

Related U.S. Application Data

(60) Continuation of application No. 15/687,502, filed on Aug. 27, 2017, now Pat. No. 11,089,955, which is a (Continued)

(51) Int. Cl.

| | |
|---|---|
| ***A61B 3/103*** | (2006.01) |
| ***A61B 3/107*** | (2006.01) |
| ***A61F 9/008*** | (2006.01) |

(52) U.S. Cl.

CPC ............ *A61B 3/1035* (2013.01); *A61B 3/107* (2013.01); *A61F 9/00825* (2013.01); (Continued)

(58) Field of Classification Search

CPC ... A61B 3/1035; A61B 3/107; A61F 9/00825; A61F 9/00827; A61F 9/00834; (Continued)

(56) References Cited

U.S. PATENT DOCUMENTS

| | | | | |
|---|---|---|---|---|
| 6,070,981 A * | 6/2000 | Mihashi | ................. | A61B 3/107 351/212 |
| 6,120,444 A * | 9/2000 | Miyakawa | ............. | A61B 3/165 600/401 |

(Continued)

FOREIGN PATENT DOCUMENTS

WO WO-2008131888 A1 * 11/2008 ............. A61B 3/107

*Primary Examiner* — Niketa Patel
*Assistant Examiner* — Sebastian X Lukjan
(74) *Attorney, Agent, or Firm* — Glen P. Belvis; Belvis Law, LLC.

(57) ABSTRACT

A laser system that includes a laser source emitting a laser beam along an axis and a keratometer. The keratometer includes a first set of individual light sources that are equally spaced from one another along a first ring and that direct a first light toward an eye and a second set of individual light sources that are equally spaced from another along a second ring and direct a second light toward the eye, wherein the first ring and said second ring are co-planar and concentric with one another about the axis. The laser system includes a telecentric lens that receives the first light and second light reflected off of the eye and a detector that receives light from the telecentric lens and forms an image. The laser system also includes a processor that receives signals from said detector representative of the image and determines an astigmatism axis of the eye based on the signals.

5 Claims, 4 Drawing Sheets

System for Measuring Corneal Astigmatism Axis of Eye Docked for Laser-Assisted Cataract Surgery Treatment

Related U.S. Application Data continuation of application No. 13/427,130, filed on Mar. 22, 2012, now abandoned, which is a continuation-in-part of application No. 13/017,499, filed on Jan. 31, 2011, now abandoned, application No. 17/375,039, filed on Jul. 14, 2021 is a continuation of application No. 15/687,501, filed on Aug. 27, 2017, now Pat. No. 11,076,756, which is a division of application No. 13/427,130, filed on Mar. 22, 2012, now abandoned.

(60) Provisional application No. 61/467,592, filed on Mar. 25, 2011, provisional application No. 61/467,622, filed on Mar. 25, 2011, provisional application No. 61/300,129, filed on Feb. 1, 2010.

(52) U.S. Cl.
CPC ...... *A61F 9/00827* (2013.01); *A61F 9/00834* (2013.01); *A61F 2009/00853* (2013.01); *A61F 2009/0087* (2013.01); *A61F 2009/00872* (2013.01); *A61F 2009/00887* (2013.01); *A61F 2009/00889* (2013.01)

(58) Field of Classification Search
CPC .... A61F 2009/00853; A61F 2009/0087; A61F 2009/00872; A61F 2009/00887; A61F 2009/00889; A61F 2009/00844
See application file for complete search history.

(56) References Cited

U.S. PATENT DOCUMENTS

| | | | | |
|---|---|---|---|---|
| 2001/0055095 A1* | 12/2001 | D'Souza | A61B 3/107 | 351/212 |
| 2009/0137988 A1* | 5/2009 | Kurtz | A61F 9/00827 | 606/4 |
| 2010/0091243 A1* | 4/2010 | Bor | A61B 3/102 | 351/219 |

* cited by examiner

SYSTEM AND METHOD FOR MEASURING AND CORRECTING ASTIGMATISM USING LASER GENERATED CORNEAL INCISIONS

This application is a continuation of Ser. No. 15/687,502 and Ser. No. 15/687,501 which are a continuation and a divisional (respectively) of Ser. No. 13/427,130 filed Mar. 22, 2012, which application claims the benefit of priority under 35 U.S.C. § 119(e)(1) of 1) U.S. Provisional Application Ser. No. 61/467,592, filed Mar. 25, 2011 and 2) U.S. Provisional Application Ser. No. 61/467,622, filed Mar. 25, 2011, and is a continuation-in-part application of U.S. patent application Ser. No. 13/017,499, filed Jan. 31, 2011, which claims the benefit of priority under 35 U.S.C. § 119(e)(1) of U.S. Provisional Application Ser. No. 61/300,129, filed Feb. 1, 2010, the entire contents of each of the above mentioned patent applications and provisional applications is incorporated herein by reference.

FIELD OF THE INVENTION

The present invention relates to a system for performing an astigmatism measurement for the purpose of correcting astigmatism. The present invention also has to do with marking the measured axis of astigmatism with a laser-created mark.

BACKGROUND

In known procedures for correcting astigmatism, such as limbal relaxing incisions, LASIK or implantation of toric IOLs, it is important to register the respective treatment or device in precise alignment relative to the eye's axis of astigmatism. The astigmatism is first measured by a benchtop corneal topographer, such as the Humphrey Atlas corneal topographer manufactured by Zeiss of Dublin, CA or a keratometer, such as the LenStar keratometer manufactured by Haag Streit of Bern, Switzerland. The patient's eye is manually marked with an ink marker to indicate the axis of astigmatism or a reference horizontal axis or other axis from which the astigmatism axis can be later referenced.

While each of the previously mentioned correction procedures is performed with the patient in a reclining position, the prior astigmatism measurement with the benchtop instrument ande and the marking of the patient's eye are performed with the patient in a sitting position. During the process of the patient being moved from the sitting position to the reclining position, cyclotorsion (rotation of the eye about its optical axis) generally occurs. The registration marker is used when the patient is in the reclining, treatment position to adjust for any rotation of the axis of astigmatism which might occur.

The use of ink marks reduces the effect of cyclotorsion on the astigmatism treatment; however, it is inconvenient—for best results, it requires a separate seating of the patient at a slit lamp—but still has limited accuracy because of the inevitable errors in manually placing the initial marks, and the "bleeding" of the marks as the tear film reacts with the marking ink.

The use of ink marks is avoided by the Placido ring measurement system described in U.S. patent application Ser. No. 13/017,499 ("the '499 application"), the entire contents of which are incorporated by reference. With the Placido ring system, the images of the reflections of Placido rings are in the form of circular or elliptical bands, with sharp, high contrast edges which allow the image analysis software in the system to accurately find the edges of each reflected circular or elliptical band. The found edges are curve fit to an ellipse. The reflections are circular (i.e. an ellipse of eccentricity equal to 0) if the cornea has no astigmatism. If the cornea does have some astigmatism, the clock angle of the minor axis of the elliptical image, gives the orientation of the axis of astigmatism. The clock angle is measured relative to a polar coordinate defined such that 0° is in the nasal direction; 90° is superior and 180°, temporal. The length of the major and minor axes of the ellipses provides the information from which the magnitude of the spherical power and cylindrical power (astigmatism) of the cornea is derived.

The Placido ring invention disclosed in the '499 application allows for the astigmatism axis to be measured while the patient is laying on a gurney under the laser so no manual measurement or marking of the eye is needed. (If a toric IOL is to be used during the corrective procedure, the laser cuts a reference mark into the capsulotomy allowing the surgeon to accurately position the clock angle of the IOL to the axis of astigmatism measured by the laser. If LRIs are to be used during the corrective procedure, the laser uses the Placido ring/keratometer measurement of axis to orient the LRIs to the correct clock angle.)

One issue regarding the Placido ring invention described in the '499 application is that it does not take into account that various preoperative measurement instruments, measuring the same parameters, generate different values of the parameters because of differences between the measurement principles, implementation of engineering, etc., of different instruments.

As an illustration of the variability in the value of measured parameters, let us take a look at a cataract procedure. In such a procedure, a number of preoperative measurements are made of the patient's eye in order to select the correct IOL for the patient. Among these measurements are measurements of the K values and axis of astigmatism of the patient's cornea. The K values are the optical power, in Diopters, of the steep axis (axis in the plane perpendicular to the optic axis which has the highest lens curvature) and shallow axis (axis in the plane perpendicular to the optic axis which has the least lens curvature). The "clock" angle of the steep and shallow axes are conventionally measured in degrees from 0° to 180° in an angular coordinate system perpendicular to and centered on the optic axis of the eye. From the point of view of an optometrist or ophthalmologist looking at the patient, 0° is to the right, on the nasal/temporal axis. The scale proceeds counterclockwise from 0° to 180°. The difference between the K value of the steep and shallow axes is the magnitude of the astigmatism of the eye. The angle of the steep axis, measured on the coordinate system described above is the axis of astigmatism. The K values and axis of astigmatism are used, along with other measurements of the eye, in one of several common IOL power formulae (ref) to determine the proper IOL optical power to be used for the patient.

A typical cataract procedure using a laser system can involve the following processes: making preoperative measurements of the patient's eye for selection of the power and other characteristics of the IOL, placement of the patient on a gurney under the laser, measuring the patient's axis of astigmatism by an integral astigmatism axis measurement system built into the laser, docking the patient's eye to the laser, performing the laser treatment, including LRIs or capsulotomy with tagged astigmatism axis if the patient's astigmatism is to be treated, retracting the laser head, removing the patient's cataractous lens and implanting an IOL is implanted. Post-operatively, the patient's surgically repaired eye is refracted by determining the amount of refractive correction needed to bring the patient's vision to its sharpest distance focus. The refraction can be measured in the same units as those used by the preoperative measurements of the patient's cornea, i.e., Diopters of curvature along the steep and shallow axes and axis of astigmatism. These values are generally converted via simple mathematical relationships to the magnitudes of the residual spherical and cylindrical power of the eye and the axis of astigmatism. However, the refraction measures ocular, rather than corneal optical power, i.e., the optical power of the whole eye including the newly implanted IOL, rather than just the corneal optical power as was measured preoperatively. In most cases, a surgeon intends to select an IOL which brings the patient's vision as close as possible to perfect focus for distance vision, i.e., to bring the patient's residual optical power to zero or near zero for both the spherical and cylindrical components of the optical power.

A cataract surgeon may monitor the post-operative refractions of his or her patients, grouped by which type or design of IOL is used. If there is a bias in the clinical outcomes for a particular type of lens, for example: patients implanted with lens Type A have an average residual spherical power of 0.5 Diopters, an adjustment parameter called a "lens constant" used in the IOL power formula is changed to allow the adjusted formula to more accurately select IOL power for future patients. The lens constant adjustment is intended to compensate for a number of factors which can affect clinical refractive outcomes. The most important of these factors is a combination of variation in surgical technique and characteristics of a particular design of IOL which affect where along the anterior/posterior axis of the eye the IOL will tend to position itself and which therefore directly influences the refractive outcome. However, the lens constant also implicitly accounts for differences in pre- and post-operative measurement techniques and, in particular, the type of instrument used to measure the K values and axis of astigmatism, which, as mentioned above, vary from instrument to instrument. For example, a keratometer which consistently measures K values a bit higher than normal would tend to cause an IOL of higher than required power to be selected for a treatment. Once this bias was detected (by post-operative measurements showing that patients tended to be overcorrected by that type of IOL as used by a particular surgeon employing that particular keratometer and other surgical procedure characteristics), the lens constant for that type of IOL (as used by that surgeon, procedure, etc.) would be adjusted to eliminate the bias.

It is helpful for this discussion to differentiate between systematic and random measurement error. Random error occurs with any type of instrumental measurement but can be reduced to an arbitrarily small magnitude by averaging a sufficient number of repeated measurements. Systematic error between instruments is due to fundamental differences in measurement technique, calibration, etc. and represents an irreducible bias between the two instruments. No amount of averaging of repeated measurements can eliminate the bias.

The foregoing process or measuring performed pre- and post-operatively and adjusting the lens constant to improve clinical refractive outcomes works well if a surgeon's surgical technique is consistent from case-to-case and if all other aspects of the surgical procedure. For example, use of a particular type of keratometer to measure K values and axis of astigmatism are likewise consistently followed. However, this latter condition is not always met. For example, a surgeon may treat patients at more than one hospital or clinic, each of which uses a different instrument to measure K values and axis of astigmatism. In this case, different lens constants could be used for each surgeon/clinic combination to correctly account for differences in refractive outcomes related to practices at each hospital or clinic, or, more likely, a single lens constant would be used across clinics even though a higher variability in clinical refractive outcomes would result.

BRIEF SUMMARY

One aspect of the present invention regards a laser system that includes a laser source emitting a laser beam along an axis and a keratometer. The keratometer includes a first set of individual light sources that are equally spaced from one another along a first ring and that direct a first light toward an eye and a second set of individual light sources that are equally spaced from another along a second ring and direct a second light toward the eye, wherein the first ring and said second ring are co-planar and concentric with one another about the axis. The keratometer also includes a telecentric lens that receives the first light and second light reflected off of the eye and a detector that receives light from the telecentric lens and forms an image of the individual light sources including the first and second lights. The keratometer further includes a processor that receives signals from said detector representative of the image and determines an astigmatism axis of the eye based on the signals.

A second aspect of the present invention regards a method of determining properties of an eye, the method including positioning an eye so that it receives a laser beam that is emitted by a laser source beam along an axis and generating first light toward the eye from a first set of individual light sources that are equally spaced from one another along a first ring. The method including generating second light toward said eye from a second set of individual light sources that are equally spaced from another along a second ring and direct a second light toward the eye, wherein the first ring and the second ring are co-planar and concentric with one another about the axis. The method further including forming an image of light reflected off of the eye from the first light and the second light and determining an astigmatism axis of the eye based on the image. The laser source, the first set of individual light sources and the second set of individual light sources are integrated in a common housing to allow the cyclotorsion of the eye which occurs between preoperative measurement, which is performed with the patient in a sitting position and at the time or surgery, when the patient is lying under the laser. The incorporation of the laser and keratometer in a common housing also allows the user to measure all patients with the same measuring device so that systematic errors in determination of IOL lens constants are avoided or reduced.

A third aspect of the present invention regards a method of treating an eye, the method including positioning an eye so that it receives a laser beam that is originally emitted by a laser source beam along an axis; and generating first light toward the eye from a first set of individual light sources that are equally spaced from one another along a first ring. The method including generating second light toward said eye from a second set of individual light sources that are equally spaced from another along a second ring and direct a second light toward the eye, wherein the first ring and the second ring are co-planar and concentric with one another about the axis. The method further including forming an image of light reflected off of the eye from the first light and the second light and determining an astigmatism axis of the eye based on the image. The method further including controlling the laser beam so that the laser beam performs a cutting of the eye based on the astigmatism axis.

One or more aspects of the present invention allow for measurement of the properties of an astigmatism axis of an eye.

One or more aspects of the present invention allow for reducing or eliminating systematic errors during measurement of the properties of an astigmatism axis of an eye.

BRIEF DESCRIPTION OF THE DRAWING

The accompanying drawings, which are incorporated herein and constitute part of this specification, and, together with the general description given above and the detailed description given below, serve to explain features of the present invention. In the drawings.

DETAILED DESCRIPTION OF THE PREFERRED EMBODIMENTS

Figure 1:
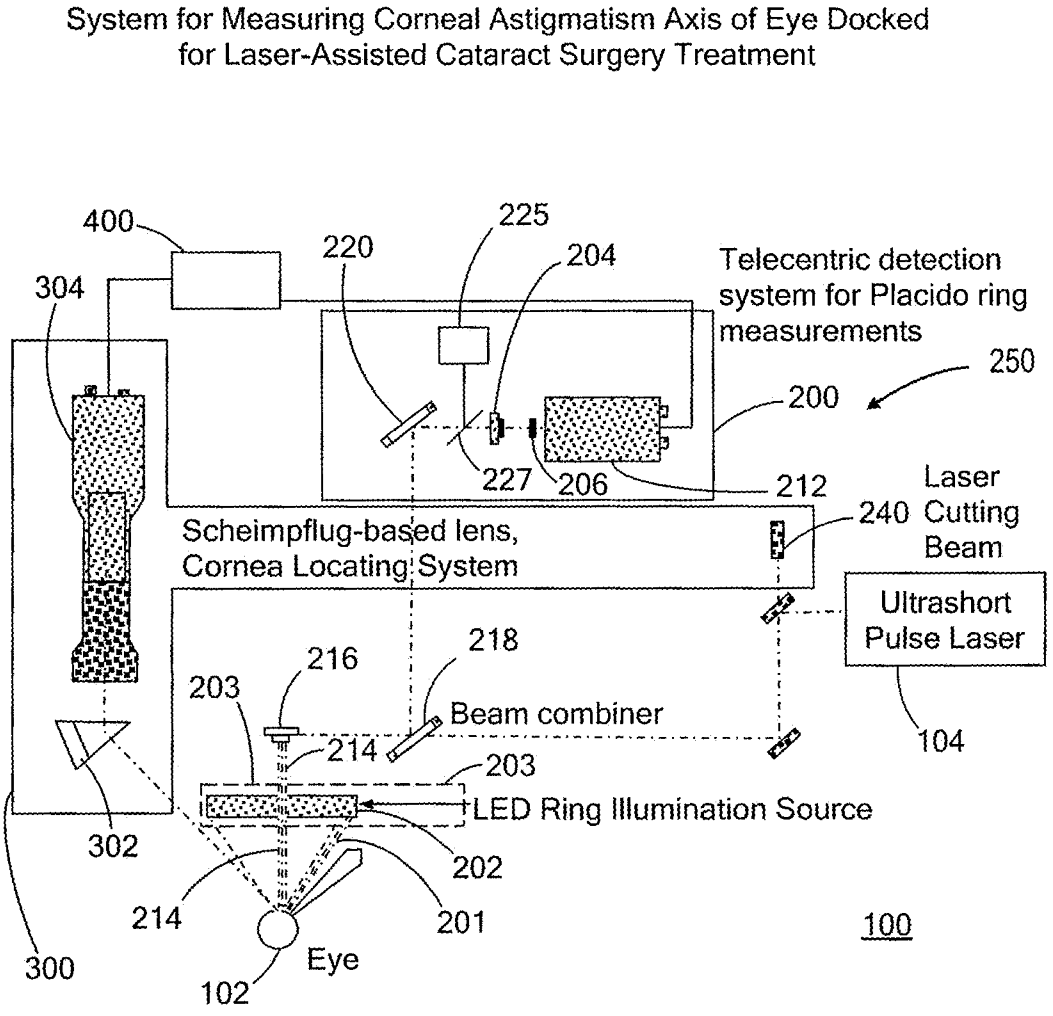
FIG. 1 schematically shows an embodiment of a measuring system for measuring the corneal astigmatism axis prior to an ophthalmological procedure being performed on the eye of a patient in accordance with the present invention.

FIG. 1 schematically shows a measuring and treatment system 100 for measuring the corneal astigmatism axis and for performing an ophthalmological procedure on the eye 102 of a patient. The system 100 includes a keratometer 250 which includes a light generator 203 (dashed lines) and a telecentric detection system 200. The light generator 203 includes two light sources, each comprising a ring of 10-20 discrete LEDs 202. The telecentric detection system 200 is used for measuring concentric rings of the LEDs 202 and for alignment of the patient's eye with the keratometer. The system 100 also includes a Scheimpflug-based lens and cornea locating system 300, and a treatment laser system that includes a treatment laser 104.

In use, the patient typically lies on a gurney or a reclining surgical chair which is rolled into position under the optical head of the treatment laser 104. The keratometer 250 and the Scheimpflug-based lens and cornea locating system 300 may be designed to work with the patient in a reclining position under the treatment laser system since in this position the cyclotorsion of the eye, which occurs when a patient who is in a sitting position (for example to allow conventional astigmatism measurements to be made) changes to a reclining position, has already occurred. It is also advantageous that the detection system 200 and the Scheimpflug-based lens and cornea locating system 300 are so located such that the patient can remain stationary for both the measurements and laser treatment, since this obviates or lessens the time consuming step of re-aligning the patient with the laser for the subsequent laser treatment.

After the corneal astigmatism axis is found using the measurement of the concentric rings of LEDs 202, a medical procedure can be performed with the laser systems described in U.S. patent application Ser. Nos. 11/337,127; 12/217,285; 12/217,295; 12/509,412; 12/509,021; 12/509,211 and 12/509,454, the entire contents of each of which are incorporated herein by reference. Possible procedures to be performed by the laser systems to correct or reduce astigmatism are the performance of limbal relaxing incisions or LASIK. Another possible procedure is the use of the treatment laser to assist in cataract removal and IOL implantation. The treatment laser is also used to create a reference mark on the anterior capsule to allow the subsequent implantation of a toric IOL to be correctly oriented with respect to the axis of astigmatism.

Operation of keratometer 250 includes having the patient lie on a patient bed in position for the laser surgery. The patient is instructed to stare at a red fixation light generated by fixation light source 225 that is housed in the telecentric detection system 200. The fixation light source 225 includes an LED which generates red light. The red light is collimated and directed to a beam combiner 227 which reflects the light to mirror 220. The red light is then redirected toward the eye of the patient so that the red light is aligned to be collinear with the axis of the laser beam generated by laser 104 and centered at the middle of the concentric rings of LEDs 202, i.e., the axis of the keratometer.

Next, the optical head of the treatment laser 104 is aligned, using a joystick that controls a 3-axis motion control system, to the patient's cornea. The optical head of the treatment laser system houses both the keratometer 250 and the Scheimpflug-based lens and cornea locating system 300 as well as the optics that are used to guide the treatment laser beam. Thus, aligning this optical head relative to the patient serves the purpose of aligning all three systems (200; 300 and treatment laser system) simultaneously relative to the patient's eye and, thus, reduces the need for time consuming re-alignments for the sequential operations. When the patient stares at the fixation light generated by fixation light source 225, and when the optical head of the treatment laser is aligned such that reflections of the two concentric rings of LEDs 202 from the patient's cornea are centered within the patient's pupil, as visualized on the telecentric camera system 200, the patient's visual axis is aligned with the keratometer 250 and treatment laser 104. A sensor, not shown, detects when the z position (position along a direction parallel to the axis of the laser beam passing through a concentric rings of LEDs 202 of light generator 203 as shown in FIG. 1) is correct for the astigmatism axis measurement; the sensor generates a signal when the eye is at the correct distance below the light generator 203. A software reticule is superimposed on the image of the eye on the telecentric camera's monitor, to assist in the assessment of centration.

After the z-position for the optical head of the treatment laser 104 is determined, and the light generator 203 is centered directly above the eye then measurement of the astigmatism axis is performed using telecentric detection system 200 for measurements of concentric rings of LEDs 202.

Telecentric system 200 is part of the keratometer 250, which is similar to the one manufactured and sold under the tradename LenStar LS-900 by Haag Streit of Bern, Switzerland. The keratometer 250 includes two sets of LEDs 202, wherein one set of 16 LEDs are equally spaced from one another along a first circle or ring. The second set of 16 LEDS 202 are equally spaced from one another along a second circle or ring. The first and second circles are co-planar and concentric with one another and concentric about the common optical axis of the fixation light source 225 and treatment laser 104. The LEDs 202 are chosen to approximate point sources of light so that the images of the reflections of the LEDs 202 from the cornea are as compact as possible and can be located on the camera image as accurately and precisely as possible. Each set of LEDs 202, as described above, is denoted as a ring source.

Figure 2:
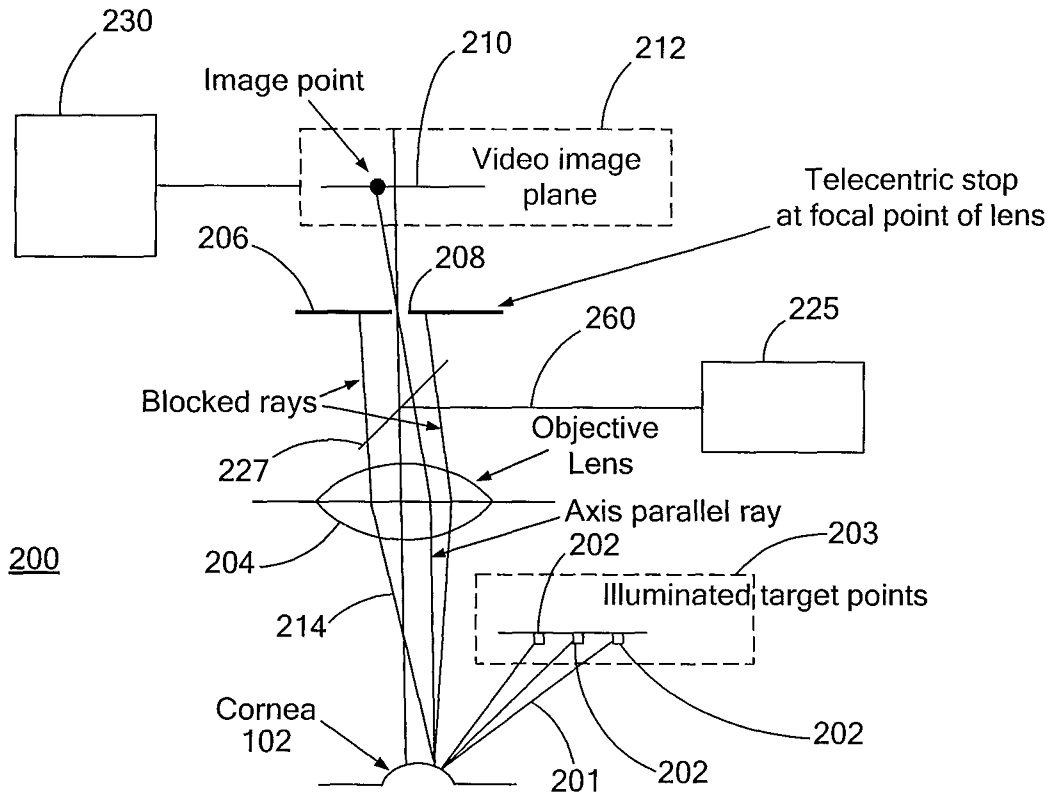
FIG. 2 schematically shows operation of an embodiment of a telecentric detection system for measurements of concentric rings of LEDs that is used with the measuring system of FIG. 1 in accordance with the present invention.
Figure 3:
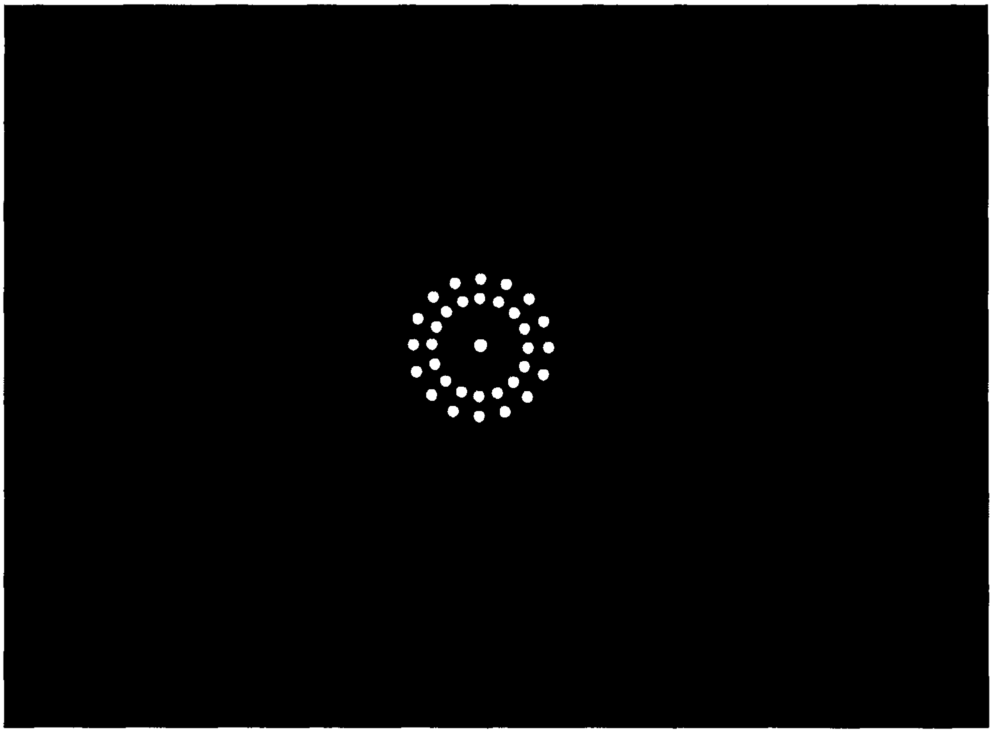
FIG. 3 shows an example of an image of light of concentric rings of LEDs as reflected off of a cornea and imaged by the telecentric detection system of FIG. 2.

Operation of keratometer 250 is understood upon a review of FIGS. 2-3. As shown in FIG. 2, red light 260 from the fixation light source 225 is directed by beam combiner 227 to the eye of the patient. When the patient stares at the red light improved alignment of the patient's eye with the axis of the keratometer 250 is achieved. While the patient stares at the red light 260, light 201 from one or more concentric ring sources of light generator 203 is directed towards the cornea of the eye 102 and then reflected light 214 is directed towards an objective and telecentric lens 204 of telecentric system 200. Note that the ring sources are concentric relative to an axis of the treatment laser beam passing through the opening of the light generator 203.

Next, the light from objective lens 204 is directed through a telecentric stop 206 that is positioned at a focal plane of the lens 204. The stop 206 includes an opening 208 positioned at a focal point of the lens 204 so that only light reflected from the cornea that was initially parallel to the axis of the objective lens is allowed to pass through the opening 208 and be received on the video image plane 210 of a detector 212. As shown in FIG. 1, additional optics, such as a beam scanning system 216, beam combiner 218 and beam splitter 220, can be used to direct the reflected light 214 toward the lens 204.

Applying the above principles to detection system 200, one or more concentric (relative to the axis of laser beam from optical head 104, which is collinear with the axis of the objective lens, 204, in FIG. 2) diverging beams of light 201 are directed from the ring sources of light source 203 toward the cornea of the eye 102. If the cornea were perfectly spherical in shape, then the beams of light 201 which reflect from the cornea into a direction parallel to that of the objective lens 204 would pass through the telecentric stop aperture 208 and form images of the discrete LEDs in the concentric rings of light on the video image plane 210. As shown in FIG. 2, a processor 230 analyzes overall image to find the positions of each discrete LED 202 from the two concentric LED rings.

For an average human cornea, with a radius of curvature of 7.8 mm, the system geometry is such that the diameters of the two concentric rings of LEDs which are imaged by the telecentric viewing system are approximately 2.3 mm and 1.65 mm, respectively, as shown in FIG. 3. For corneas of different radii of curvature, the size of the reflected rings will differ and a determination of the size of the image of the reflected concentric rings of LEDs 202 on the telecentric camera detector 212 is used to determine the radius of curvature of the cornea. If the cornea is astigmatic, the cornea's shape will deviate slightly from that of a perfect sphere in such a way as to cause the image of the reflection of the ring sources to have a nearly elliptical shape. Based on the measurement of the positions of the centroids of the discrete LEDs 202 which include the two concentric rings, the shape and size of the two circular or elliptical LED patterns formed on the video image plane 210 is determined by the processor 230, using standard numerical methods such as those described in Turuwhenua, Jason, "An Improved Low Order Method for Corneal Reconstruction", Optometry and Vision Science, Vol. 85, No. 3, March 2008, pp. E211-E218. From these data, the curvature of the cornea along the direction of a steep and shallow meridian, i.e. the "K values", and the "clock" angle of the the axes of the steep and shallow meridian with respect to the standard eye-fixed coordinate system, described above, can be determined by a processor. If only the astigmatism axis is needed, a simple method of extracting it from the reflected images is to determine the angles of the semi-major axes of the ellipses using a simple least squares curve fitting technique.

The choice of geometry to cause the reflected diameters of the rings of LEDs 202 to fall into the roughly 1.5 mm to 3 mm range results in an astigmatism (and corneal shape) measurement that is accurate for the central 3 mm of the cornea. Such a central region-biased measurement of optical power results in better vision for most patients over a variety of lighting conditions and patient activities (ref). (For some eyes the optical power of the cornea is quite non-uniform; the average optical power over a small central region may differ significantly from the average power averaged over, for example, a 6 mm to 7 mm diameter circular region centered on the optical axis of the cornea.)

Note that the incorporation of a high quality keratometer 250 into a femtosecond ophthalmic laser, being used as laser 104, addresses the problem of higher variability in clinical refractive outcomes resulting from variability in measurement of patients' corneal K values and axes of astigmatism arising from use of different types of instruments for that purpose. For purposes here, femtosecond ophthalmic laser means a laser used in ophthalmology for making incisions in the eye using the mechanism of photodisruption. Such lasers have pulse widths that are generally between 100 femtoseconds and 10,000 femtoseconds. The improvement in clinical outcomes can be achieved in one of two ways. First, the built-in keratometer could be used for measuring the K values and axes of astigmatism of all patients at the time of the procedure and those results be used for determination of the spherical and cylindrical power in the IOL to be used for treatment. In this way, all variability due to variation in measurement of these parameters with different types of optical power measuring instruments would be eliminated. The lens constants determined by the method described above would account for other factors, such as surgical technique/IOL characteristics, but would not be subject to variability associated with optical power measurement.

Alternatively, the built-in keratometer could be used in conjunction with a standalone keratometer of the same type of design to reduce variability in the measurement of axis of astigmatism. This use of the built-in keratometer in conjunction with a stand-alone keratometer of the same design for pre-operative measurements, recognizes that the measurement of K values and axis of astigmatism depend on the type of optical design used. Although the K values and axis of astigmatism measured on a given eye by all types of measuring instruments will be similar, differences in reported values may vary significantly. Instrument-to-instrument variation may be due to the region of the cornea measured by an instrument (for example one instrument may measure optical power over the central 2.5 mm of the cornea; another may measure over 3.5 mm), the type of illumination source used (for example Placido rings versus rings of discrete LEDs), how the data is analyzed, etc. The effect of an error of as little as 10° in treatment of astigmatism axis is a 30% under correction of the astigmatism (A M Fea, et al, Eye 20, 764-768 (2006)).

In this use of the present invention, the corneal optical power of a patient undergoing a cataract treatment with associated correction of astigmatism would be measured on a particular type of standalone keratometer, for example the keratometer sold under the tradename LenStar LS900 by Haag Streit of Bern, Switzerland). The K values of the pre-operative measurement would be used for determination of IOL spherical and cylindrical optical power. At the time of surgery, with the patient on a gurney under the femtosecond laser, the built-in keratometer would be used to measure the axis of astigmatism of the patient's cornea. As described above, this measurement of axis, with the patient lying horizontally, is needed to compensate for cyclotorsion of the patient's eye between the pre-operative keratometer measurement made with the patient in a sitting position and that measured in the operative position of the patient, lying on a gurney. The built-in keratometer would be designed in all significant aspects to measure K values and axis of astigmatism in the same manner and to produce identical results (except for those associated with cyclotorsion) as the pre-operative, standalone keratometer. Therefore any bias in measurement of astigmatism axis from one type of measurement instrument to another is eliminated and the treated axis is as near as possible to the correct astigmatism axis of the patient is used to treat the astigmatism with the best possible clinical refractive outcome.

Note that the previously mentioned bias in measurement would also be reduced or eliminated in the case where a Placido ring system as described in U.S. patent application Ser. No. 13/017,499 is incorporated into a treatment laser and such a built-in system is used to measure corneal K values and axes properties of the eye in a manner as described above with respect to the built-in keratometer. And as above, such a built-in Placido ring system, used in conjunction with a standalone Placido ring system of essentially the same design could be used in the same manner and with the same benefits as is described above the built in and standalone keratometer systems.

After the measurements of the rings of LEDs 202 previously described are made by systems 200 and 300, the optical head of treatment laser 104 is moved directly upward, out of the way, to allow access to the patient's eye 102 for application of a suction ring. In operation, a suction ring (not shown) is applied manually to the patient's eye 102. After the suction ring is applied, the optical head of treatment laser 104 is docked, using the previously described joystick. Since the patient's eye 102 has not been moved and since the treatment laser 104 and the astigmatism measuring systems 200 and 300 are aligned to each other, the treatment laser 104 can now be used to correct or reduce the astigmatism of the eye 102, based on the previously described astigmatism axis determination and/or the corneal shape determination, using limbal relaxing incisions (LRIs) or LASIK, aligning the astigmatism treatment to the measured axis of astigmatism.

The above described alignment system and process can also be applied to procedures that involve implanting a toric intraocular lens (IOL) to treat astigmatism. Note that IOLs are synthetic lenses implanted into the capsular bag in the eye, after a cataractous lens is removed. The IOL restores vision by replacing partially opaque cataractous lens with a clear lens of appropriate power. A conventional IOL has only spherical power. A toric IOL has both spherical and cylindrical power and can thus correct astigmatism in the eye.

Figure 4:
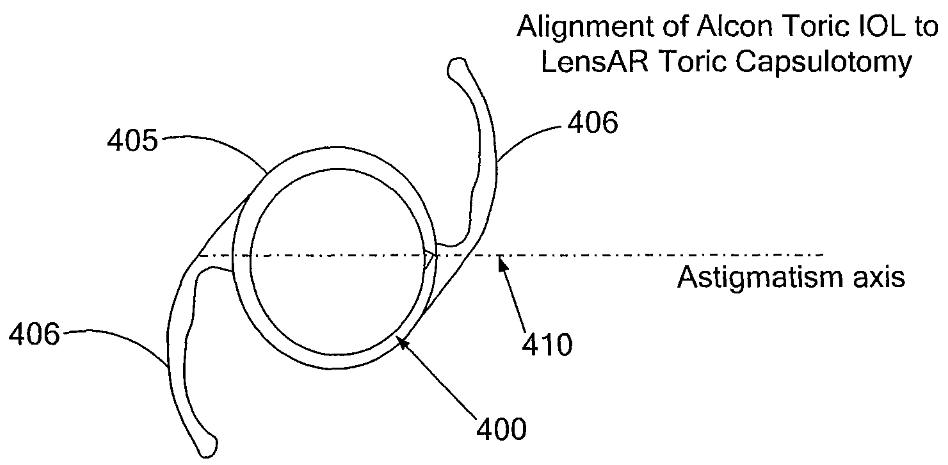
FIG. 4 shows picture of a common toric intraocular lens (IOL) implanted in an eye after the corneal astigmatism axis of the eye has been determined and marked using a treatment laser, using the measuring system of FIG. 1 in accordance with the present invention.

In the case when a toric IOL is to be subsequently implanted to treat astigmatism, the treatment laser 104 can be used to mark the axis of astigmatism for later use in aligning the axis of astigmatism 410 (shown in FIG. 4) of the IOL 405 (with haptics 406 used for anchoring IOL 405 in the capsular bag), with the marked axis of astigmatism of the eye 102.

Figure 5:
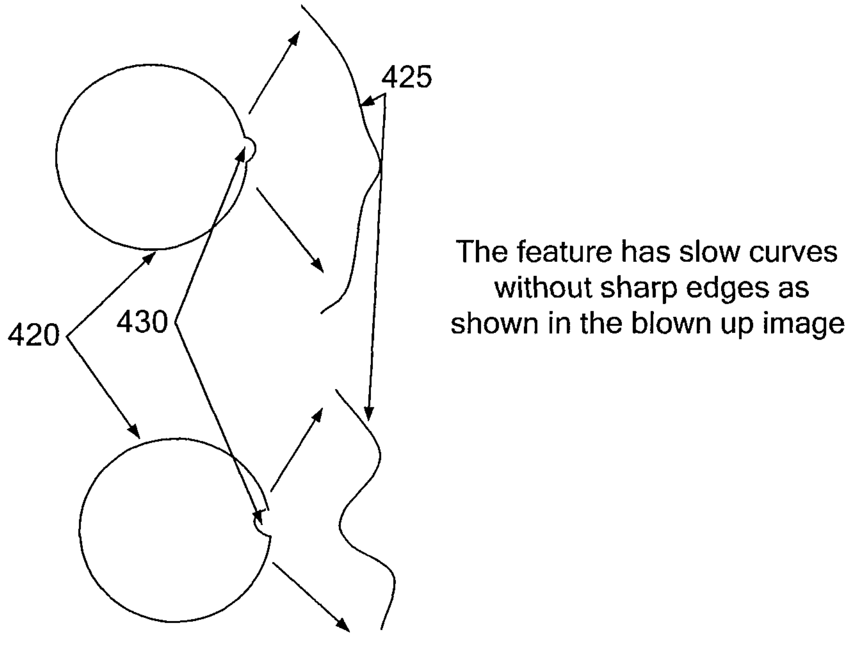
FIG. 5 schematically shows laser cut capsulotomy openings in the anterior crystalline lens capsule cut with a "tag" to mark the axis of astigmatism that is measured by the measuring system of FIG. 1 in accordance with the present invention.

In cataract procedures, a round opening is manually torn or cut by a laser in the crystalline lens anterior capsule. The cataractous lens is removed through the opening and an IOL is placed into the capsular bag, generally centered behind the capsular opening. The treatment laser 104 can be used to cut a small "tag" as part of the circular capsulotomy 400. The "tag" provides a visible reference mark along which the axis of astigmatism of the IOL 410 can be aligned. As shown in FIG. 5, the "tags" 430 in the capsular openings can be positioned inwardly or outwardly. The "tag" is cut in a smooth curve along the capsulotomy cut to avoid risk of radial capsular tears during the cataract procedure. Possible smooth shapes of the "tags" are shown schematically in close-up 425. This method of marking the astigmatism axis by incorporating a "tag" in the capsulotomy allows the astigmatism mark, i.e. the "tag" to be ideally placed for use in aligning the astigmatism axis of the IOL. The "tag" is in the immediate vicinity of the astigmatism mark on the IOL and may in fact be directly over the astigmatism axis mark on the IOL, avoiding any errors in registration which might occur when aligning the IOL mark with, for example, an ink mark on the sclera, a considerable distance from the IOL. In summary, the "tag" provides a visual marker so that the surgeon implanting a toric IOL can line up the astigmatism axis of the IOL with marked axis of astigmatism of the eye 102.

To avoid any possible distortion of the astigmatism axis of the eye 102 which might occur when the a suction ring is placed on the eye 102 for docking with the optical head of the treatment laser 104, a small mark, for example a line, could be made by the laser in the center of the lens capsule immediately after the astigmatism axis was measured as described above. Then, after affixing the suction ring and docking the eye 102 to the optical head, the marks in the center of the capsule could be used, either manually or using automatic image recognition techniques built into a computer program, to set the position of the "tag"-marked laser-cut capsulotomy for use in the toric IOL implantation.

Still another alternate method of marking the astigmatism axis with the treatment laser would entail shooting several laser shots, either at full or reduced energy at the position of the astigmatism axis at the limbus to make a persistent visible reference mark.

Since the x, y position of the optical head of the treatment laser 104 is pre-aligned during the astigmatism axis measurement process, very little adjustment is needed to dock the optical head to the suction ring. Note that the telecentric viewing system 200 is also used as a general viewing system, to assist the laser system associated with the optical head of the treatment laser 104 when the optical head is docked to the suction ring.

Use of the measuring system 250 built in to the above described laser system 100 is advantageous. For example, the measuring system 250 would allow measuring the astigmatism axis in situ, while the patient is lying on the treatment bed, just in advance of the laser treatment—thus eliminating the need for pre-operative eye marks. In the case of performing limbal relaxing incisions, the automatic measurement of the astigmatism axis by system 100 increases the accuracy of the placement of the limbal relaxing incisions, thereby improving the efficacy of the treatment. The method can also be used in conjunction with the laser to mark the astigmatism axis for cyclotorsional registration of a toric IOL.

Despite the benefits of the method in convenience and more accurate, automatic placement of the treatment axis for astigmatism, and the advantage of reducing clinical outcome variability by consistently using a built in measurement system, or built in measurement system in conjunction with a pre-operative standalone system of the same design, to eliminate variability in clinical outcomes caused by determination of IOL, lens constants with different measurement systems of different design types, there is no laser astigmatism treatment device which currently incorporates an astigmatism measuring system into the device. The present invention eliminates the need for manually marking the eye and circumvents the inaccuracies inherent in manual placing of marks and the dispersion of the ink marks by the eye's tear film; in addition, it provides a means to more accurately determine IOL lens constants to reduce clinical outcome variability. The integral astigmatism measurement, in combination with use of marks made by the treatment laser can be used to mark the axis of astigmatism for later registration of a toric IOL or for any subsequent refractive treatment of the eye requiring knowledge of the axis of astigmatism.

Since the measuring device is built into the optical head of the treatment laser 104, the alignment of the measuring 100 to the eye 102 reduces the time needed later to align the eye to the laser treatment system. The system 100 also makes dual use of a camera 212 and ring light sources 202 for both the astigmatism measurement and for general viewing of the eye during the eye docking and lasing parts of the procedure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A laser system configured to eliminate systematic error in performing a cataract procedure, the system comprising:

a) a means for determining an axis of astigmatism of an eye having a cataractous lens;

b) a means for providing a femtosecond laser beam for performing a capsulotomy comprising a tag aligned with the axis of astigmatism;

c) the tag having slow curves without sharp edges, whereby the risk of radial capsular tears is avoided;

d) the means for determining the axis of astigmatism and the means for providing the femtosecond laser beam are integrated with a common housing;

e) whereby systematic errors in determination of an IOL lens constant are eliminated.

2. The laser system of claim 1, wherein the tag is positioned inwardly of the capsular opening.

3. The laser system of claim 1, wherein the tag is positioned outwardly of the opening.

4. The laser system of claim 2, wherein the capsular opening is circular.

5. The laser system of claim 3, wherein the capsular opening is circular.

* * * * *